(12) United States Patent
Kohayakawa

(10) Patent No.: US 6,757,555 B2
(45) Date of Patent: Jun. 29, 2004

(54) OPHTHALMOLOGIC APPARATUS

(75) Inventor: Yoshimi Kohayakawa, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/074,545

(22) Filed: Feb. 12, 2002

(65) Prior Publication Data
US 2002/0118338 A1 Aug. 29, 2002

(30) Foreign Application Priority Data
Feb. 19, 2001 (JP) ........................................ 2001-042084

(51) Int. Cl.[7] ................................................ A61B 5/00
(52) U.S. Cl. ........................ 600/318; 600/324; 600/504
(58) Field of Search .............................. 600/309, 310, 600/318–324, 340, 504; 351/209, 210

(56) References Cited

U.S. PATENT DOCUMENTS

| | | | | |
|---|---|---|---|---|
| 4,579,430 A | * | 4/1986 | Bille | 600/318 |
| 4,856,891 A | * | 8/1989 | Pflibsen et al. | 351/210 |
| 5,090,416 A | * | 2/1992 | Ogino et al. | 600/504 |
| 5,291,885 A | * | 3/1994 | Taniji et al. | 600/310 |

* cited by examiner

Primary Examiner—Eric F. Winakur
Assistant Examiner—David J. McCrosky
(74) Attorney, Agent, or Firm—Morgan & Finnegan LLP

(57) ABSTRACT

An ophthalmologic apparatus has a first light source for the measurement of a blood flow velocity by the Doppler shift method, and a second light source which differs in wavelength from the first light source and used for tracking of a blood vessel to be measured. This apparatus can simultaneously obtain a blood oxygen concentration from the difference in reflectance between two light sources from the measurement position on the blood vessel.

9 Claims, 3 Drawing Sheets

OPHTHALMOLOGIC APPARATUS

BACKGROUND OF THE INVENTION

1. Field of the Invention

The present invention relates to an ophthalmologic apparatus used in, for example, ophthalmic hospital to examine the fundus of an eye.

2. Related Background Art

Conventionally, following apparatuses have been used in accordance with purposes: a fundus blood flow measurement apparatus for measuring a blood flow velocity or rate on the eye fundus, an oximeter for measuring an oxygen concentration in the blood in the eye fundus, a fundus camera for imaging a wide range on the eye fundus, and the like.

In order to achieve all these purposes, therefore, three ophthalmologic apparatuses are required. That is, the corresponding installation space and facility cost are required. In addition, a subject must move to ophthalmologic apparatuses in accordance with purposes, imposing burdens on each examiner who handles measurement and the subject.

In addition, since pieces of diagnostic information associated with each other are obtained by the respective ophthalmologic apparatuses, it is not easy to measure a blood flow and blood oxygen concentration at the same position on the fundus. Furthermore, it is impossible to measure them at the same time.

SUMMARY OF THE INVENTION

It is an object of the present invention to provide an ophthalmologic apparatus which solve these problems and can simultaneously measure a blood flow velocity or rate and a blood oxygen concentration. It is another object of the present invention to provide a single ophthalmologic apparatus which can additionally take eye fundus image.

An ophthalmologic apparatus according to the present invention is characterized by comprising at least two of an image taking system which takes eye fundus image by projecting a light beam on the fundus through an optical system, a blood flow detection system which detects a blood flow by projecting a light beam on the fundus through the optical system and detecting light reflected by the fundus, and a blood oxygen concentration detection system which detects a blood oxygen concentration by projecting, through the optical system, a light beam on the portion of the fundus on which the light beam is projected by the blood flow detection system, and detecting light reflected by the portion.

This apparatus is characterized by comprising display means for displaying at least two of the resultant image and the measurement results obtained by the blood flow detection system and blood oxygen concentration detection system.

The above and other objects, features, and advantages of the present invention will be apparent from the following detailed description in conjunction with the accompanying drawings and the appended claims.

DETAILED DESCRIPTION OF THE PREFERRED EMBODIMENTS

The present invention will be described in detail below on the basis of the embodiments shown in the accompanying drawings.

Figure 1:
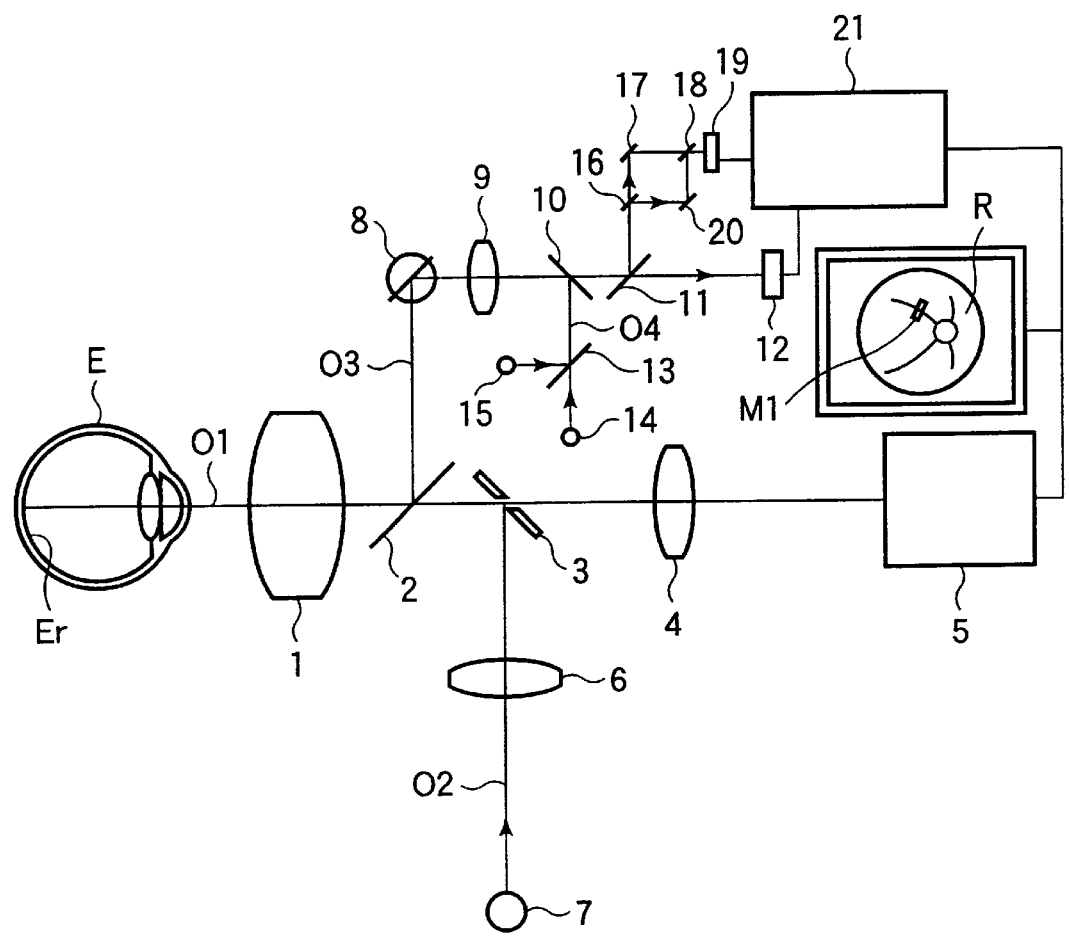
FIG. 1 is a view showing the arrangement of the first embodiment.

FIG. 1 is a view showing the optical configuration of the first embodiment. An ophthalmologic apparatus according to this embodiment has the function of measuring a blood flow as a blood flow velocity or rate on the fundus and the function of measuring a blood oxygen concentration as the oxygen concentration in the oxyhemoglobin of the blood, in addition to the function of taking a fundus image.

On an optical path O1 in front of an eye E to be examined, the following components are arranged: an objective lens 1, a dichroic mirror 2 serving as a light beam splitting member which transmits an illumination light beam and reflects a measurement light beam, an apertured mirror 3 which is nearly conjugate to the pupil, a lens 4, and a video camera 5 serving as an image pickup means. A lens 6 and a light source 7 which emits a near-infrared illumination light beam having a wavelength of about 800 to 900 nm are arranged on an optical path O2 in the incidence direction of the apertured mirror 3.

On an optical path O3 for measurement in the reflecting direction of the dichroic mirror 2, the following components are arranged: a galvanometric mirror 8, a lens 9, a half mirror 10 serving as a light beam splitting member, a dichroic mirror 11, and a photoelectric sensor 12 which is a line array sensor CCD nearly conjugate to the fundus.

In addition, on an optical path O4 in the incidence direction of the half mirror 10, the following components are arranged: a dichroic mirror 13, and a light source 14 which is nearly conjugate to the fundus and emits a green laser beam having a wavelength of 530 nm. A light source 15 which is nearly conjugate to the fundus and emits a red laser beam having a wavelength of 670 mn is placed in the incidence direction of the dichroic mirror 13.

In the incidence direction of the dichroic mirror 11, the following components are arranged: a half mirror 16 which is nearly conjugate to the pupil, reflects a light beam on one side of an optical path, and transmits a light beam on the other side, a mirror 17, a dichroic mirror 18, and a photoelectric sensor 19 nearly conjugate to the fundus. A mirror 20 is placed in the reflecting direction of the half mirror 16. The above dichroic mirror 18 is placed in the reflecting direction of the mirror 20.

The outputs of the photoelectric sensors 12 and 19 are connected to a signal processing part 21 having an arithmetic part, memory, and the like. The outputs of the video camera 5 and signal processing part 21 are connected to a monitor 22 formed by a CRT.

A light beam from the light source 7 illuminates a fundus Er of the eye E to be examined through the lens 6, apertured mirror 3, dichroic mirror 2, and objective lens 1. The light reflected by the fundus Er comes into the video camera 5 through the objective lens 1, dichroic mirror 2, apertured mirror 3, and lens 4. The lens 4 forms, on the video camera 5, the fundus image formed by the objective lens 1. A fundus image R is displayed on the monitor 22.

Light beams from the light sources 14 and 15 are projected on a predetermined portion of the fundus Er through the dichroic mirror 13, half mirror 10, lens 9, galvanometric mirror 8, dichroic mirror 2, and objective lens 1. The light reflected by the fundus Er returns along the optical paths O1 and O3 and comes into the dichroic mirror 11.

The dichroic mirror 11 transmits a green light beam from the light source 14, and reflects a red light beam from the light source 15. Therefore, the light beam transmitted through the dichroic mirror 11 comes into the photoelectric sensor 12, and the light beam reflected by the dichroic mirror 11 is split into two optical paths through the half mirror 16. The split light beams are merged by the dichroic mirror 18 and come into the photoelectric sensor 19. Signals from the photoelectric sensors 12 and 19 are input to the signal processing part 21. The signal processing part 21 performs signal processing, computation, and control required for measurement. A measurement mark M1 indicating a measurement portion of the fundus is displayed on the monitor 22.

In this case, a blood flow is measured by the Doppler shift method. More specifically, light beams reflected by a blood flow in different directions are subjected to different Doppler shifts. Therefore, a blood flow velocity is obtained by detecting this shift amount, and a blood flow rate is calculated by multiplying the blood flow velocity by the blood vessel diameter. At this time, the measurement portion of the fundus Er is illuminated with a green light beam from the light source 14 to check the position of the blood vessel by using the photoelectric sensor 12. If the line of sight of the eye E to be examined has slightly moved, the measurement portion is adjusted by pivoting the galvanometric mirror 8 to be automatically held on the optical path O3.

The red light beam emitted from the light source 15 and reflected by the fundus is extracted from different positions on the pupil through the half mirror 16. These light beams are then caused to interfere with each other to obtain a beat signal corresponding to the wavelength shift. The beat signal is then frequency-analyzed by the signal processing part 21 to calculate a blood flow velocity. A blood vessel diameter is then obtained from the blood vessel detected by the photoelectric sensor 12. A blood flow rate is calculated by multiplying this blood flow diameter by the blood flow velocity.

A blood oxygen concentration is measured by using the spectral absorption characteristics between oxidized hemoglobin and unoxidized hemoglobin. More specifically, a green light beam from the light source 14 causes no difference in spectral absorption characteristics. In contrast to this, a red light beam from the light source 15 is scarcely absorbed by oxidized hemoglobin but is considerably absorbed by unoxidized hemoglobin. Therefore, the ratio of light reflected by oxidized hemoglobin to light reflected by unoxidized hemoglobin is obtained to obtain a blood oxygen concentration which is the ratio of oxidized hemoglobin to unoxidized hemoglobin.

In this case, a reflectance with respect to a green light beam is obtained from the amount of light emitted from the light source 14 and the amount of light received by the photoelectric sensor 12, and a reflectance with respect to a red light beam is obtained from the amount of light emitted from the light source 15 and the amount of light received by the photoelectric sensor 19, thereby calculating a blood oxygen concentration from the ratio between the reflectances. The oxygen supply amount of the blood vessel is calculated from this blood oxygen concentration and the blood flow rate that has already been obtained. These calculated values are then displayed on the monitor 22 or output to a printer (not shown).

In the first embodiment, a blood flow and blood oxygen concentration, which have been measured by different apparatuses, can be measured by a single apparatus. This makes it possible to reduce the installation space and facility cost. In addition, since the subject and examiner need not move, the burdens on them decrease.

In addition, if light beams from the light sources 14 and 15 are simultaneously projected on the same portion of the fundus Er, a blood flow and blood oxygen concentration on the same portion can be simultaneously measured. This improves the value of diagnostic information and shortens the diagnosis time.

In the first embodiment described above, a blood oxygen concentration is measured by using two light beams from the light sources 14 and 15. However, it can be measured with three light beams, additionally using a light beam from the light source 7. In this case, a near-infrared light beam having a wavelength of 800 to 900 nm from the light source 7 does not cause much difference in light beam absorbance between oxidized hemoglobin and unoxidized hemoglobin. For this reason, the intensity of a video signal from the video camera 5 is input to the signal processing part 21 to obtain a reflectance from the relationship between the intensity of the video signal and the intensity of a light beam from the light source 7, and a blood oxygen concentration is calculated from the ratios between reflectances with respect to three light beams.

In addition, a blood vessel wall, retina, or the like mirror-reflects a light beam, and hence has no light beam wavelength selectivity. Therefore, appropriate spectral reflection characteristics are assumed for these light beams. With this operation, in using three light beams having different wavelengths, even if a light beam having a different spectral reflection characteristic mixes with them, measurement can be performed upon removal of this light beam.

In the first embodiment, the light sources 7, 14, and 15 and photoelectric sensors 12 and 19 are used for both measurements of a blood flow and measurement of a blood oxygen concentration. However, different members can be used for the respective measurements.

In addition, if an electronic flash is added as a fundus illumination light source, the image pickup means 5 can pick up a fundus image with visible light. Furthermore, by printing a mark M indicating a measurement portion of a fundus image in image taking operation, the specific portion of the fundus at which the measurement value is obtained can be recorded. Moreover, a combination of a fundus image taking means and blood flow measurement or a fundus image taking means and blood oxygen concentration measurement can also be implemented.

Figure 2:
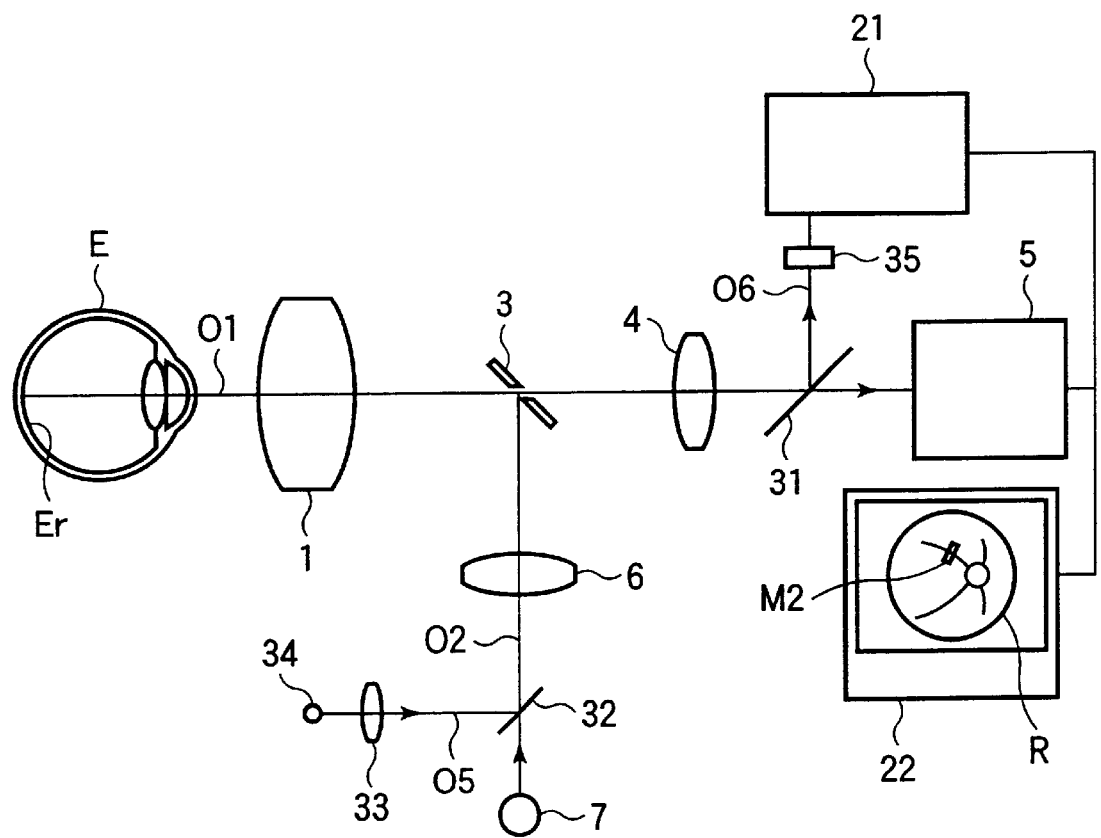
FIG. 2 is a view showing the arrangement of the second embodiment.

FIG. 2 shows the optical configuration of the second embodiment. An ophthalmologic apparatus according to the second embodiment also has the function of measuring a blood flow and the function of measuring a blood oxygen concentration, in addition to the function of observing a fundus image. The same reference numerals as in FIG. 1 denote the same parts in FIG. 2.

On an optical path O1 in front of an eye E to be examined, the following components are arranged: an objective lens 1, an apertured mirror 3, a lens 4, a dichroic mirror 31 which reflects a red light beam, and a video camera 5. A lens 6, a dichroic mirror 32 which reflects a red light beam, and a light source 7 are arranged on an optical path O2 in the incidence direction of the apertured mirror 3. A lens 33 and a light source 34 which emits a red laser beam having a wavelength of 650 to 750 nm are arranged on an optical path O5 in the incidence direction of the dichroic mirror 32.

A photoelectric sensor 35 which is an area array sensor conjugate to the fundus is placed on an optical path O6 in the reflecting direction of the dichroic mirror 31. The output of the photoelectric sensor 35 is connected to a signal processing part 21. The outputs of the video camera 5 and signal processing part 21 are connected to a monitor 22.

A red light beam from the light source 34 comes into the dichroic mirror 32 through the lens 33. The red light beam reflected by the dichroic mirror 32 illuminates a predetermined portion of a fundus Er through the lens 6, apertured mirror 3, and objective lens 1. The light reflected by the fundus Er comes into the dichroic mirror 31 through the objective lens 1, apertured mirror 3, and lens 4. This light is then reflected by the dichroic mirror 31 and incident on the photoelectric sensor 35. A measurement mark M2 indicating a measurement area covered by the photoelectric sensor 35 is displayed on the monitor 22.

A blood flow is measured by using the laser speckle method. More specifically, when a coherent red light beam from the light source 34 is incident on a diffuser such as the fundus Er, a so-called random speckle pattern due to multiple reflection is generated. This speckle pattern moves upon movement of the diffuser, and the moving speed is associated with the flow of the diffuser, i.e., a blood cell. The changing speed of a speckle pattern is therefore obtained by reading out a signal from the photoelectric sensor 35 at about 500 Hz and calculating the correlation between adjacent pictures, thereby obtaining a value corresponding to a blood flow velocity. In addition, a blood flow map is generated by measuring other portions as well as the blood vessel.

A blood oxygen concentration is measured by using the ratio between the reflectance with respect to a near-infrared light beam from the light source 7 and the reflectance with respect to a red light beam from the light source 34. More specifically, a red light beam from the light source 34 is not much absorbed by saturated oxyhemoglobin but is considerably absorbed by unoxidized hemoglobin. In contrast to this, a near-infrared light beam from the light source 7 is absorbed by both oxidized hemoglobin and unoxidized hemoglobin. This light beam is absorbed by oxidized hemoglobin slightly more than by unoxidized hemoglobin. Therefore, reflectances with respect to these light beams are detected from the intensity of a signal from the photoelectric sensor 35 and the intensity of a video signal from the video camera 5, and an oxygen concentration is calculated by the signal processing part 21, thereby obtaining a blood oxygen concentration map.

The second embodiment can also simultaneously measure a blood flow and blood oxygen concentration and calculate an oxygen supply amount by multiplying the blood flow rate and the oxygen concentration as well as obtaining a fundus image. In addition, as in the first embodiment, a blood flow and blood oxygen concentration can be measured with a higher precision by using three light beams. In this case, a light source for emitting a light beam having different wavelength and one photoelectric sensor are added.

Figure 3:
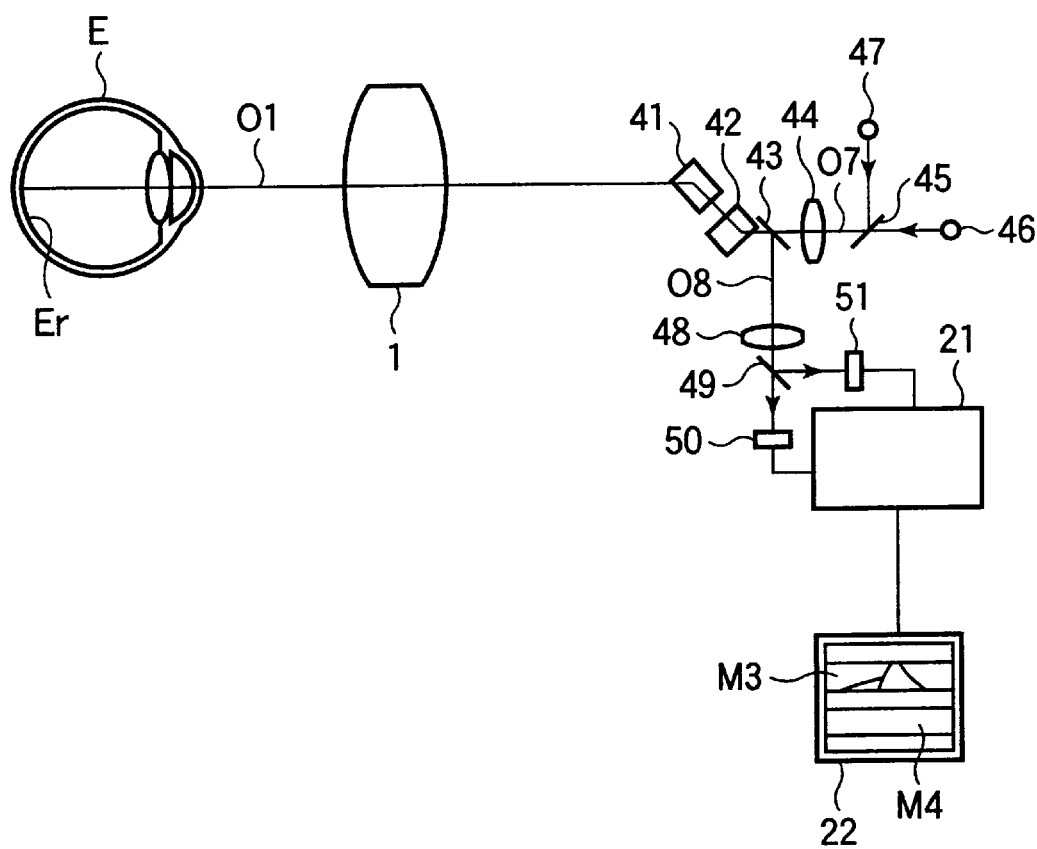
FIG. 3 is a view showing the arrangement of the third embodiment.

FIG. 3 shows the optical configuration of the third embodiment. An ophthalmologic apparatus according to the third embodiment has the functions of measuring a blood flow and blood oxygen concentration. The same reference numerals as in FIGS. 1 and 2 denote the same parts in FIG. 3.

On an optical path O1 in front of an eye E to be examined, the following components are arranged: an objective lens 1, a galvanometric mirror 41 which performs sub-scanning operation, a resonance mirror 42 which performs main scanning operation, and a half mirror 43 which is located near the resonance mirror 42 and conjugate to the pupil. On an optical path O7 behind the half mirror 43, the following components are arranged: a lens 44, a dichroic mirror 45 which splits a red light beam having a wavelength of 670 nm and a near-infrared light beam having a wavelength of 800 nm, and a light source 46 which is conjugate to the fundus and emits a laser beam having a wavelength of 800 nm. A light source 47 which is conjugate to the fundus and emits a laser beam having a wavelength of 670 nm is placed in the incidence direction of the dichroic mirror 45.

A lens 48, dichroic mirror 49, and photoelectric sensor 50 are arranged on an optical path O8 in the reflecting direction of the half mirror 43. A photoelectric sensor 51 is placed in the reflecting direction of the dichroic mirror 49.

The outputs of the photoelectric sensors 50 and 51 are connected to a signal processing part 21. The output of the signal processing part 21 is connected to a monitor 22.

The light sources 46 and 47 project light beam spots on a predetermined portion of a fundus Er through the dichroic mirror 45, lens 44, half mirror 43, resonance mirror 42, galvanometric mirror 41, and objective lens 1.

The light reflected by the fundus Er is reflected by the half mirror 43 and incident on the dichroic mirror 49 through the lens 48. The light beam transmitted through the dichroic mirror 49 comes into the photoelectric sensor 50. The light beam reflected by the dichroic mirror 49 comes into the photoelectric sensor 51. Signals from the photoelectric sensors 50 and 51 are input to the signal processing part 21. As a consequence, a blood flow map M3 and blood oxygen concentration map M4 at a measurement portion of the fundus Er are displayed on the monitor 22.

Meanwhile, a measurement light beam is scanned by the resonance mirror 42 over 100 in the lateral direction at 4 kHz, and is also scanned by the galvanometric mirror 41 over 2.50 in the longitudinal direction at 64 Hz, thereby inputting two-second data in the memory of the signal processing part 21.

In measuring a blood flow, a light beam from the light source 47 illuminates a predetermined portion of the fundus Er, and the light reflected by the fundus Er comes into the photoelectric sensor 51. The signal processing part 21 performs fast Fourier transform on a signal from the photoelectric sensor 51 which corresponds to each predetermined portion, thereby calculating a Doppler shift and measuring a blood flow velocity.

In measuring a blood oxygen concentration, the light source 46 is turned on in addition to the light source 47. A light beam from the light source 46 spot-illuminates the same portion as that illuminated by the light source 47. The light beams reflected by the fundus Er are respectively received by the photoelectric sensors 50 and 51, and the signal processing part 21 detects the intensities of the respective light beams. The signal processing part 21 obtains a reflectance with respect to a light beam having a wavelength of 670 nm and a reflectance with respect to a light beam having a wavelength of 800 nm from the detected light intensities, and measures a blood oxygen concentration from the ratio between these reflectances. The third embodiment can also measure a blood flow and blood oxygen concentration at once.

Note that the first and third embodiments have exemplified the ophthalmologic apparatuses each having an optical system for detecting a blood flow and an optical system for detecting a blood oxygen concentration. However, an optical system for detecting a blood flow or an optical system for detecting a blood oxygen concentration may be juxtaposed with a non-mydriatic fundus camera.

As has been described above, since the ophthalmologic apparatus according to the present invention has at least two functions of the following three functions: the function of imaging a fundus image, the function of measuring a fundus blood flow, and the function of measuring the oxygen saturated value of a fundus blood flow, a reduction in installation space and facility cost can be attained. In addition, the burdens on a subject and examiner in measurement decrease.

In addition, if light beams are simultaneously projected on the same portion of the fundus, a blood oxygen concentration and blood flow at the same portion can be simultaneously measured. This improves the value of diagnostic information and shortens the diagnosis time.

What is claimed is:

1. An ophthalmologic apparatus comprising:
   (1) blood flow velocity detection means including first projection means for projecting a first light beam on a fundus, first light-receiving means for receiving reflected light of the first light beam, and blood flow velocity measurement means for measuring a blood flow velocity on the basis of an output from said first light-receiving means; and
   (2) blood oxygen concentration detection means including second projection means for projecting a second light beam which differs in wavelength from the first light beam on the fundus, second light-receiving means for receiving reflected light of the second light beam, and arithmetic means for computing a blood oxygen concentration by using an output from said first light-receiving means and an output from said second light-receiving means.

2. An apparatus according to claim 1, further comprising a galvanometric mirror which deflects the first and second light beams, and
   said galvanometric mirror being deflected to perform tracking on the basis of an output from said second light-receiving means so as to make the first light beam track a measurement position of a blood vessel to be measured.

3. An apparatus according to claim 1, wherein the blood flow and blood oxygen concentration are detected at the same position on the fundus.

4. An apparatus according to claim 1, further comprising:
   image pickup means for picking up the fundus image of the eye to be examined; and
   display means for displaying the pickup image.

5. An apparatus according to claim 4, wherein a value associated with a measured blood flow velocity and a value associated with a blood oxygen concentration are displayed on said display means, together with the pickup image.

6. An ophthalmologic apparatus comprising:
   (1) blood flow velocity measurement means for measuring a blood flow velocity on the basis of reflected light of a first light beam projected on a blood vessel of a fundus; and
   (2) blood oxygen concentration measurement means for measuring a blood oxygen concentration on the basis of the first reflected light beam and reflected light of a second light beam projected on the blood vessel of the fundus which differs in wavelength from the first light beam.

7. An apparatus according to claim 6, wherein the second light beam is used to detect a position of a blood vessel to be measured.

8. An apparatus according to claim 6, further comprising a first optical system which projects/receives the first light beam, and a second optical system which projects/receives the second light beam, said first and second optical systems have a common portion.

9. An apparatus according to claim 7, further comprising a first optical system which projects/receives the first light beam, and a second optical system which projects/receives the second light beam, said first and second optical systems have a common portion.

* * * * *

UNITED STATES PATENT AND TRADEMARK OFFICE
CERTIFICATE OF CORRECTION

PATENT NO. : 6,757,555 B2
DATED : June 29, 2004
INVENTOR(S) : Yoshimi Kohayakawa It is certified that error appears in the above-identified patent and that said Letters Patent is hereby corrected as shown below:

Column 6,
Line 35, please delete "100" and insert therefore -- $10º$ --.

Signed and Sealed this

Fifth Day of April, 2005

JON W. DUDAS
*Director of the United States Patent and Trademark Office*